US00PP19864P2

(12) United States Plant Patent
Pierce

(10) Patent No.: US PP19,864 P2
(45) Date of Patent: Mar. 31, 2009

(54) ***CALIBRACHOA* PLANT NAMED 'CAL ORANG08'**

(50) Latin Name: ***Calibrachoa* sp.**
Varietal Denomination: CAL ORANG08

(75) Inventor: Robert Pierce, Watsonville, CA (US)

(73) Assignee: Goldsmith Seeds Inc., Gilroy, CA (US)

( * ) Notice: Subject to any disclaimer, the term of this patent is extended or adjusted under 35 U.S.C. 154(b) by 0 days.

(21) Appl. No.: 12/080,151

(22) Filed: Mar. 31, 2008

(51) Int. Cl.
*A01H 5/00* (2006.01)

(52) U.S. Cl. ..... Plt./413
(58) Field of Classification Search ..... Plt./413
See application file for complete search history.

*Primary Examiner*—Annette H Para
(74) *Attorney, Agent, or Firm*—C. A. Whealy

(57) ABSTRACT

A new and distinct cultivar of *Caliachoa* plant named 'Cal Orang08', characterized by its mounding and outwardly spreading to trailing plant habit; freely branching habit; dense and full plants; early and freely flowering habit; numerous bright orange-colored flowers; and good garden performance.

1 Drawing Sheet

Botanical designation: *Calibrachoa* sp.
Cultivar denomination: 'CAL ORANG08'.

BACKGROUND OF THE INVENTION

The present invention relates to a new and distinct cultivar of *Calibrachoa*, botanically known as *Calibrachoa* sp. and hereinafter referred to by the name 'Cal Orang08'.

The new *Calibrachoa* is a product of a planned breeding program conducted by the Inventor in Gilroy, Calif. The objective of the breeding program is to create new *Calibrachoa* cultivars with uniform plant habit and numerous attractive flowers.

The new *Calibrachoa* originated from a cross-pollination made by the Inventor in August, 2004 in Gilroy, Calif. of the *Calibrachoa* sp. cultivar Cal Goldey, disclosed in U.S. Plant Pat. No. 17,303, as the female, or seed, parent with a proprietary selection of *Calibrachoa* sp. identified as code number 1285, not patented, as the male, or pollen, parent. The new *Calibrachoa* was discovered and selected by the Inventor as a single flowering plant within the progeny of the stated cross-pollination in a controlled environment in Gilroy, Calif. in April, 2005.

Asexual reproduction of the new *Calibrachoa* by vegetative cuttings in a controlled environment in Gilroy, Calif. since April, 2005 has shown that the unique features of this new *Calibrachoa* are stable and reproduced true to type in successive generations.

SUMMARY OF THE INVENTION

The cultivar Cal Orang08 has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Cal Orang08'. These characteristics in combination distinguish 'Cal Orang08' as a new and distinct cultivar of *Calibrachoa*:

1. Mounding and outwardly spreading to trailing plant habit.
2. Freely branching habit; dense and full plants.

3. Early and freely flowering habit.
4. Numerous bright orange-colored flowers.
5. Good garden performance.

The new *Calibrachoa* can be compared to plants of the female parent, the cultivar Cal Goldey. Plants of the new *Calibrachoa* differ from plants of the cultivar Cal Goldey in the following characteristics:

1. Plants of the new *Calibrachoa* are more prostrate in plant habit than plants of the cultivar Cal Goldey.
2. Plants of the new *Calibrachoa* have more flowers in the center than plants of the cultivar Cal Goldey.
3. Plants of the new *Calibrachoa* and the cultivar Cal Goldey differ in flower color as plants of the cultivar Cal Goldey have gold-colored flowers.

Plants of the new *Calibrachoa* can be compared to plants of the male parent selection. Plants of the new *Calibrachoa* differ from plants of the male parent selection in the following characteristics:

1. Plants of the new *Calibrachoa* are more freely branching than plants of the male parent selection.
2. Plants of the new *Calibrachoa* flower earlier than plants of the male parent selection.
3. Plants of the new *Calibrachoa* and the male parent selection differ in flower color as plants of the male parent selection have salmon-colored flowers.

Plants of the new *Calibrachoa* can be compared to plants of the cultivar Cal Oran, disclosed in U.S. Plant Pat. No. 16,737. In side-by-side comparisons conducted in Hillscheid, Germany, plants of the new *Calibrachoa* differed from plants of the cultivar Cal Oran in the following characteristics:

1. Plants of the new *Calibrachoa* were more compact than plants of the cultivar Cal Oran.
2. Plants of the new *Calibrachoa* were more freely branching than plants of the cultivar Cal Oran.
3. Plants of the new *Calibrachoa* had narrower and brighter green-colored leaves than plants of the cultivar Cal Oran.
4. Plants of the new *Calibrachoa* had smaller flowers than plants of the cultivar Cal Oran.

BRIEF DESCRIPTION OF THE PHOTOGRAPH

The accompanying colored photograph illustrates the overall appearance of the new *Calibrachoa*, showing the colors as true as it is reasonably possible to obtain in colored reproductions of this type. Colors in the photograph may differ slightly from the color values cited in the detailed botanical description which accurately describe the colors of the new *Calibrachoa*. The photograph comprises a close-up view of a typical flowering plant of 'Cal Orang08'.

DETAILED BOTANICAL DESCRIPTION

The aforementioned photograph and following observations, measurements and values describe plants grown in Hillscheid, Germany under commercial practice during the summer in an outdoor nursery. Plants used for the photograph were grown in 15-cm containers for about 16 weeks. Plants used for the description were grown in 25-cm hanging basket containers for about seven months. In the following description, color references are made to The Royal Horticultural Society Colour Chart, 2001 Edition, except where general terms of ordinary dictionary significance are used.

Botanical classification: *Calibrachoa* sp. cultivar Cal Orang08.

Parentage:

*Female, or seed parent.*—*Calibrachoa* sp. cultivar Cal Goldey, disclosed in U.S. Plant Pat. No. 17,303.

*Male, or pollen, parent.*—Proprietary selection of *Calibrachoa* sp. identified as code number 1285, not patented.

Propagation:

*Type.*—By vegetative cuttings.

*Time to initiate and develop root.*—About 18 to 23 days.

*Root description.*—Fibrous; color, close to 155D.

Plant description:

*Plant and growth habit.*—Mounding and outwardly spreading to trailing plant habit. Freely branching habit with about eight primary lateral branches each with about four to five secondary lateral branches; full and dense plants. Vigorous growth habit.

*Plant height.*—About 20 cm to 25 cm.

*Plant diameter.*—About 60 cm to 70 cm.

Lateral branch description:

*Length.*—About 30 cm to 40 cm.

*Diameter.*—About 3 mm to 4 mm.

*Interode length.*—About 2 cm to 3.5 cm.

*Strength.*—Strong; flexible.

*Aspect.*—Initially upright to outwardly spreading to trailing.

*Texture.*—Densely hirsute.

*Color.*—Close to 143C.

Foliage description:

*Arrangement.*—Alternate, simple.

*Length.*—About 3.5 cm to 4 cm.

*Width.*—About 1.3 cm to 1.8 cm.

*Shape.*—Elliptic.

*Apex.*—Obtuse to rounded.

*Base.*—Attenuate.

*Margin.*—Entire.

*Texture, upper and lower surfaces.*—Hirsute; more dense at the margins and midrib.

*Venation pattern.*—Pinnate; arcuate.

*Color.*—Developing foliage, upper surface: Close to 137D. Developing foliage, lower surface: Close to 139C. Fully expanded foliage, upper surface: Close to 137C; venation, close to 145B. Fully expanded foliage, lower surface: Close to 139C; venation, close to 145A.

*Petioles.*—Length: About 2 mm. Diameter: About 2 mm. Texture, upper and lower surfaces: Hirsute; more dense at the margins and midrib. Color, upper and lower surfaces: Close to 144C.

Flower description:

*Flower arrangement and habit.*—Single salverform flowers arranged singly arising from upper leaf axils. Freely flowering habit with usually about 120 to 150 flowers developing per plant. Flowers not persistent. Flowers face mostly outwardly.

*Fragrance.*—None detected.

*Natural flowering season.*—Plants of the new *Calibrachoa* initiate and develop flowers about eight to ten weeks after planting. Plants flower continuously during the summer in Hillscheid, Germany.

*Flower longevity.*—Individual flowers last about five to eight days on the plant.

*Flower diameter.*—About 3.7 cm to 4 cm.

*Flower length (height).*—About 3.7 cm to 4 cm.

*Corolla tube length.*—About 1.6 cm to 1.8 cm.

*Flower bud.*—Shape: Oblong, elongate. Length: About 2.5 cm to 2.7 cm. Diameter: About 7 mm. Color: Close to 12C; towards the apex, 39A to 39B.

*Corolla.*—Arrangement: Five petals fused at the base and opening into a flared trumpet; flowers star-shaped. Petal shape: Roughly obovate. Petal apex: Truncate to slightly retuse. Petal margin: Entire; weakly undulate. Petal texture, upper surface: Papillose, glabrous; satiny. Petal texture, lower surface: Hirsute. Color: Petal, when opening, upper surface: Close to 40C. Petal, when opening, lower surface: Close to 33D. Petal, fully opened, upper surface: Close to 32B; towards the throat, close to 45A; venation, close to 45A. With development, color becoming closer to 32C; towards the throat, close to 44A. Color of some flowers eventually becoming closer to 39B. Petal, fully opened, lower surface: Close to 33D; random patches, close to 51C to 51D. Throat: Close to 7A. Tube: Closeto 11B.

*Calyx.*—Arrangement: One star-shaped calyx tube with five sepals fused at the base per flower. Sepal length: About 1.5 cm to 1.6 cm. Sepal width: About 3 mm. Sepal shape: Lanceolate to ligulate. Sepal apex: Rounded. Sepal margin: Entire. Sepal texture, upper and lower surfaces: Densely hirsute; more dense at margins and midrib. Color, upper surface: Close to between 137D and 143A. Color, lower surface: Close to 137D.

*Peduncles.*—Length: About 1.5 cm to 2.2 cm. Diameter: About 1 mm. Strength: Moderately strong; flexible. Texture: Hirsute. Color: Close to 144B.

*Reproductive organs.*—Stamens: Quantity/arrangement: About five per flower. Filament length: About 1 cm to 1.4 cm. Filament diameter: About 1 mm. Filament color: Close to 150D. Anther shape: Reniform, two-parted. Pollen amount: Moderate. Pollen color: Close to 8A. Pistils: Quantity: One per flower. Pistil length: About 1.2 cm. Style color: Close to 145D. Stigma shape: Ovate. Stigma color: Close to 145A. Ovary color: Close to 145D.

*Seeds/fruits.*—Seed and fruit development have not been observed.

Garden performance:

Plants of the new *Calibrachoa* have been observed to have good garden performance and tolerate wind, rain and temperatures ranging from about 5° C. about 30° C.

Pathogen/pest resistance; Plants of the new *Calibrachoa* have not been observed to be resistant to pathogens and pests common to *Calibrachoa*.

It is claimed:

1. A new and distinct *Calibrachoa* plant named 'Cal Orang08' as illustrated and described.

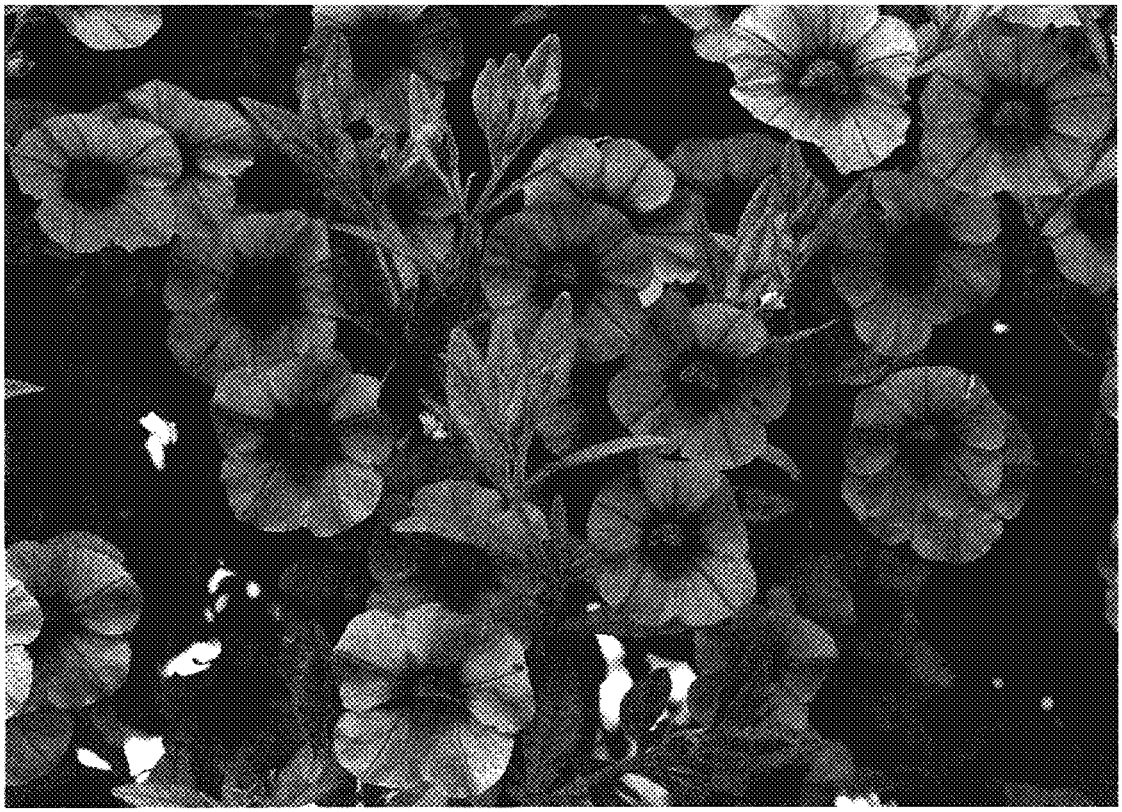

* * * * *